(12) United States Patent
DiClaudio

(10) Patent No.: US 10,595,894 B2
(45) Date of Patent: Mar. 24, 2020

(54) BALLOON CATHETERS AND METHODS THEREOF

(71) Applicant: C.R. Bard, Inc., Murray Hill, NJ (US)

(72) Inventor: Karen A. DiClaudio, Tempe, AZ (US)

(73) Assignee: C.R. BARD, INC., Tempe, AZ (US)

( * ) Notice: Subject to any disclaimer, the term of this patent is extended or adjusted under 35 U.S.C. 154(b) by 0 days.

(21) Appl. No.: 16/469,206

(22) PCT Filed: Dec. 12, 2017

(86) PCT No.: PCT/US2017/065839
§ 371 (c)(1),
(2) Date: Jun. 13, 2019

(87) PCT Pub. No.: WO2018/111889
PCT Pub. Date: Jun. 21, 2018

(65) Prior Publication Data
US 2019/0380738 A1    Dec. 19, 2019

Related U.S. Application Data

(60) Provisional application No. 62/435,223, filed on Dec. 16, 2016.

(51) Int. Cl.
*A61M 25/10* (2013.01)
*A61B 17/3207* (2006.01)
(Continued)

(52) U.S. Cl.
CPC . *A61B 17/320725* (2013.01); *A61M 25/0052* (2013.01); *A61M 25/0054* (2013.01);
(Continued)

(58) Field of Classification Search
CPC .. A61B 17/320725; A61B 2017/00557; A61B 2017/00477; A61M 25/0052;
(Continued)

(56) References Cited

U.S. PATENT DOCUMENTS

| 5,904,679 A * | 5/1999 | Clayman ................ A61B 17/22 604/114 |
| 2005/0177130 A1 | 8/2005 | Konstantino et al. |

(Continued)

OTHER PUBLICATIONS

Appeal Board Decision; USPTO; Patent Trial and Appeal Board; Ex parte Karen DiClaudio; Appeal 2019-000981; U.S. Appl. No. 14/727,231; dated Dec. 19, 2019.

*Primary Examiner* — Katherine M Rodjom
(74) *Attorney, Agent, or Firm* — King & Schickli, PLLC

(57) ABSTRACT

Provided herein in some embodiments is a catheter including an elongate body with a polymeric portion and a metallic portion; a balloon over at least some of the polymeric portion; a coupler formed over or between the polymeric and metallic portions; and one or more scoring wires. The metallic portion can include a spiral-cut portion configured to prevent elongation and kinking of the elongate body. The one or more scoring wires can be fixed to and extend from a tip at a distal end of the elongate body, over the balloon, through the polymeric portion of the elongate body, through the coupler, and to the metallic portion of the elongate body. The one or more scoring wires can be fixed to an internal surface of the spiral-cut portion or formed from the spiral-cut portion.

22 Claims, 13 Drawing Sheets

Figure 1:
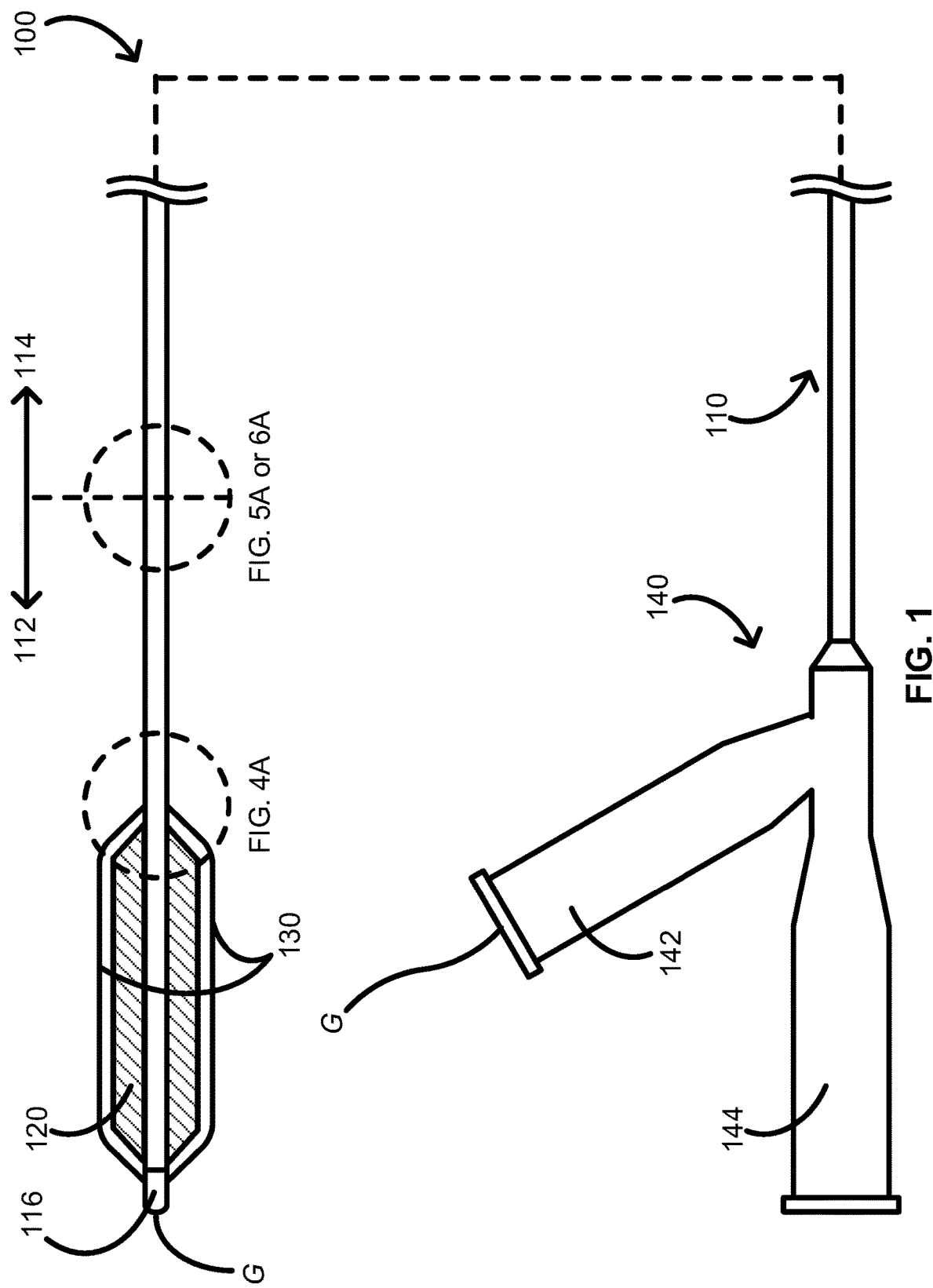

(51) Int. Cl.
    *A61M 25/01*     (2006.01)
    *A61M 25/09*     (2006.01)
    *A61M 25/00*     (2006.01)
    *A61B 17/00*     (2006.01)

(52) U.S. Cl.
    CPC ........ *A61M 25/0108* (2013.01); *A61M 25/09* (2013.01); *A61M 25/104* (2013.01); *A61M 25/10181* (2013.11); *A61B 2017/00477* (2013.01); *A61B 2017/00557* (2013.01); *A61M 2025/0059* (2013.01); *A61M 2025/0183* (2013.01); *A61M 2025/109* (2013.01); *A61M 2025/1081* (2013.01)

(58) Field of Classification Search
    CPC ............ A61M 25/0053; A61M 25/104; A61M 25/0054; A61M 25/1036; A61M 25/1034; A61M 2025/109; A61M 2025/0059; A61M 2025/1086
    See application file for complete search history.

(56) References Cited

U.S. PATENT DOCUMENTS

| | | | |
|---|---|---|---|
| 2008/0045928 A1* | 2/2008 | Simpson | ........... A61M 25/1036 604/525 |
| 2014/0277002 A1 | 9/2014 | Grace | |
| 2014/0324079 A1 | 10/2014 | Silvestro | |

* cited by examiner

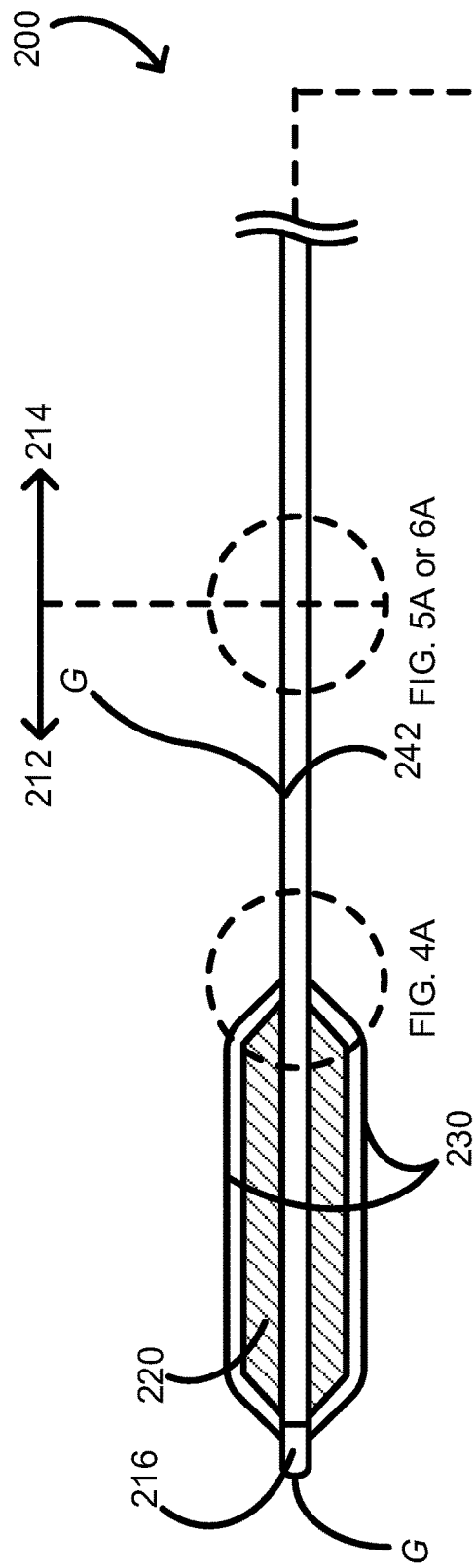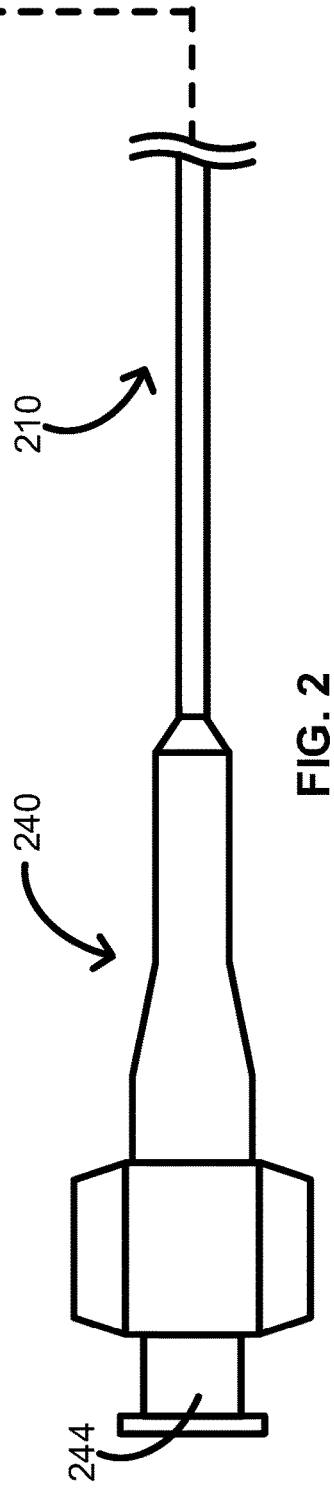
FIG. 2

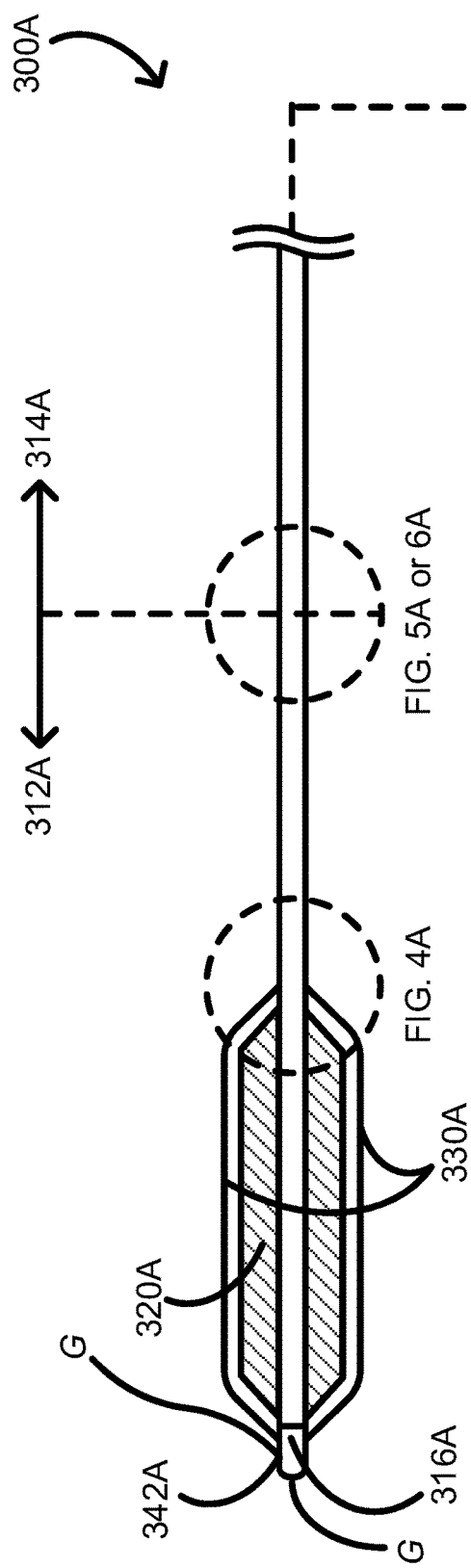
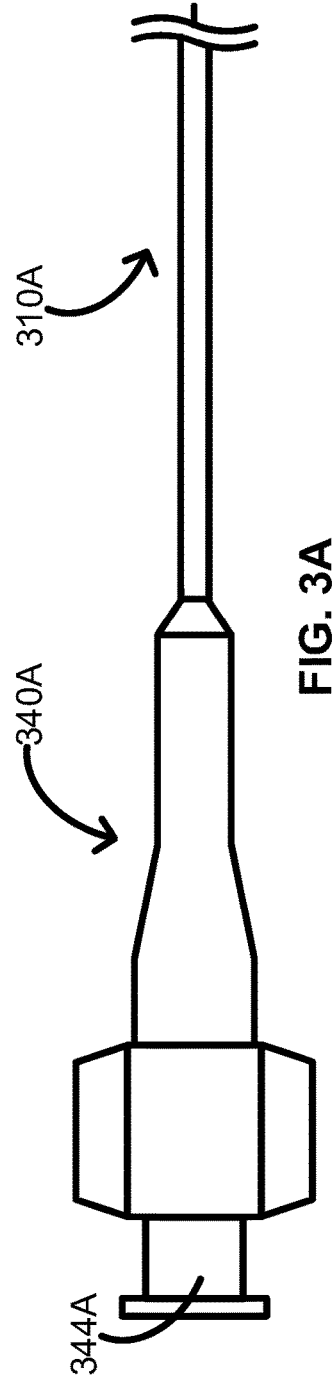
FIG. 3A

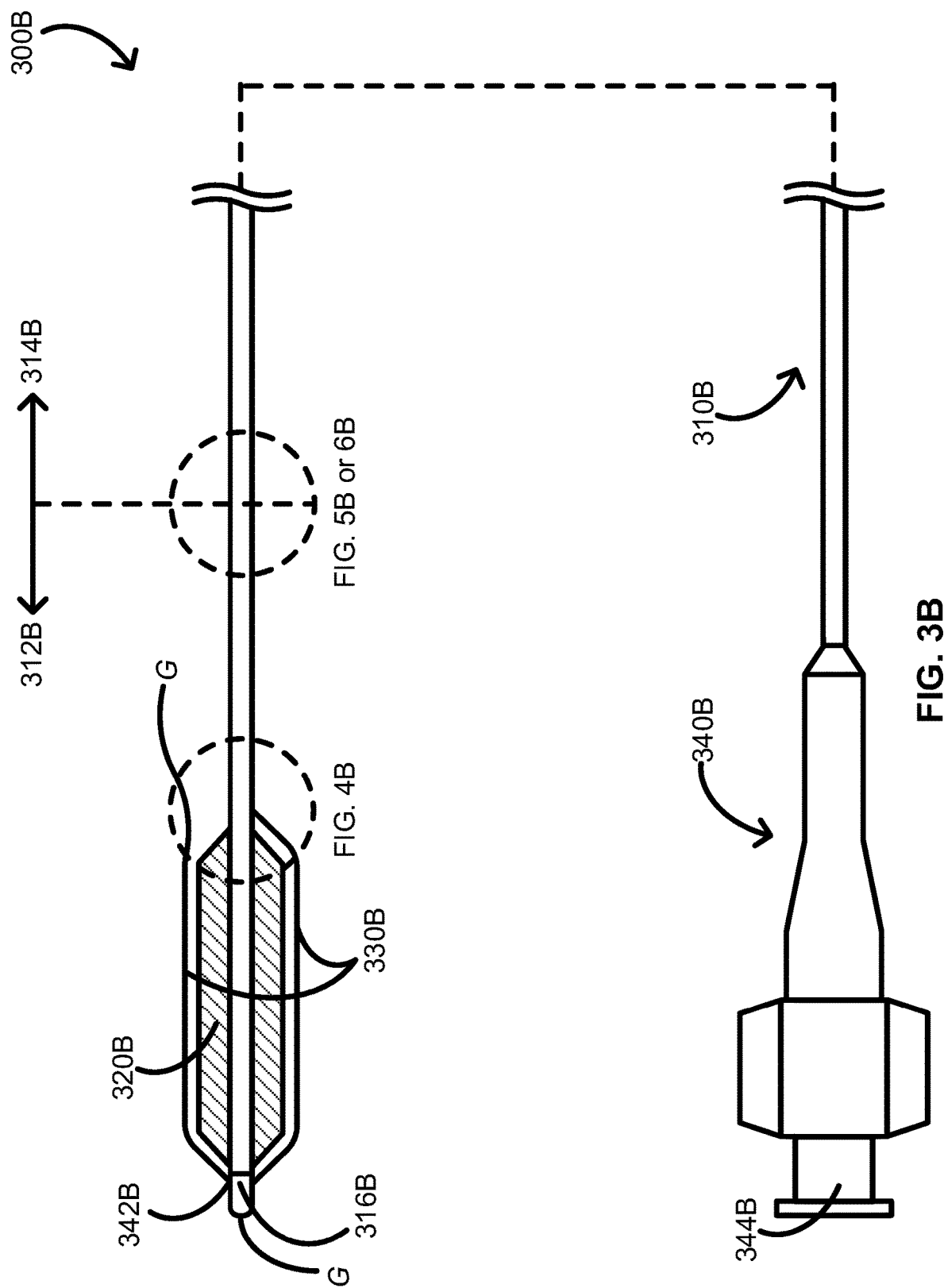

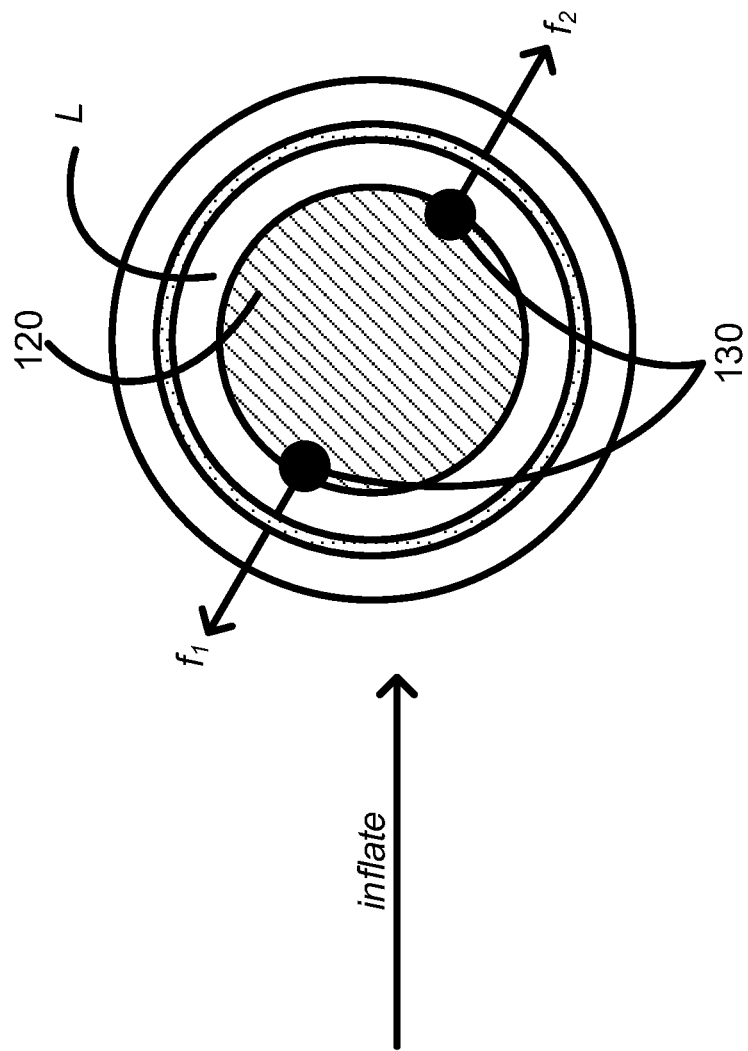
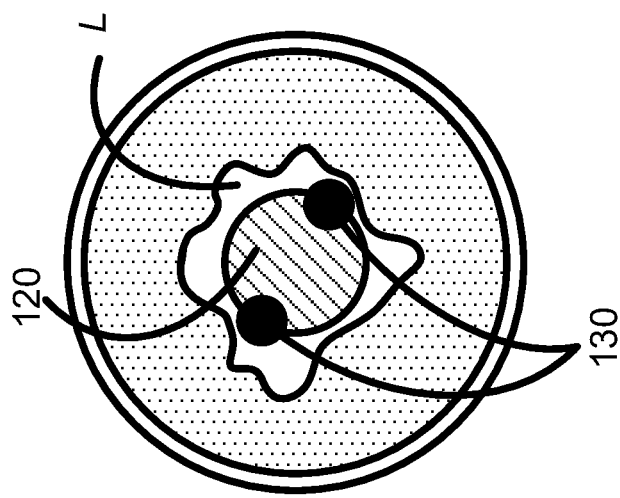
FIG. 7

US 10,595,894 B2

BALLOON CATHETERS AND METHODS THEREOF

PRIORITY

This application claims the benefit of priority to U.S. Provisional Application No. 62/435,223, filed Dec. 16, 2016, which is incorporated in its entirety into this application.

FIELD

This application generally relates to balloon catheters and methods thereof.

BACKGROUND

Atherosclerosis is characterized by one or more intravascular lesions formed in part of plaque including blood-borne substances such as fat, cholesterol, and calcium. An intravascular lesion such as an arterial lesion can form on a wall of an arterial lumen and build out across the lumen to an opposite wall thereof. A last point of patency often occurs at a boundary between the arterial lesion and the opposite wall of the arterial lumen.

Surgical procedures for atherosclerosis such as balloon angioplasty can be used to restore patency and blood flow lost to the one or more intravascular lesions. Because early balloons could cause wall trauma by non-uniformly unfolding during inflation, changes have been made to balloon catheters to control balloon inflation and the forces imparted thereby. However, such changes are often not isolated to the balloons of such balloon catheters. Other balloon-catheter components and the performance thereof can be affected as well. Accordingly, there is a need to control balloon inflation and the forces imparted thereby while maintaining integrity in other balloon-catheter components. Provided herein in some embodiments are systems and methods that address the foregoing.

SUMMARY

Provided herein in some embodiments is a catheter including an elongate body with a polymeric portion and a metallic portion; a balloon over at least some of the polymeric portion; a coupler formed over or between the polymeric and metallic portions; and one or more scoring wires. The metallic portion can include a spiral-cut portion configured to prevent elongation and kinking of the elongate body. The one or more scoring wires can be fixed to and extend from a tip at a distal end of the elongate body, over the balloon, through the polymeric portion of the elongate body, through the coupler, and to the metallic portion of the elongate body. The one or more scoring wires can be fixed to an internal surface of the spiral-cut portion or formed from the spiral-cut portion.

These and other features of the concepts provided herein may be better understood with reference to the drawings, description, and appended claims.

DRAWINGS

FIG. 1 provides a schematic illustrating an over-the-wire balloon catheter including at least a pair of scoring wires in accordance with some embodiments.

FIG. 2 provides a schematic illustrating a rapid-exchange balloon catheter including at least a pair of scoring wires in accordance with some embodiments.

FIG. 3A provides a schematic illustrating a short rapid-exchange balloon catheter including at least a pair of scoring wires in accordance with some embodiments.

FIG. 3B provides a schematic illustrating a short rapid-exchange balloon catheter including a scoring wire and a guidewire and in accordance with some embodiments.

Figure 4A:
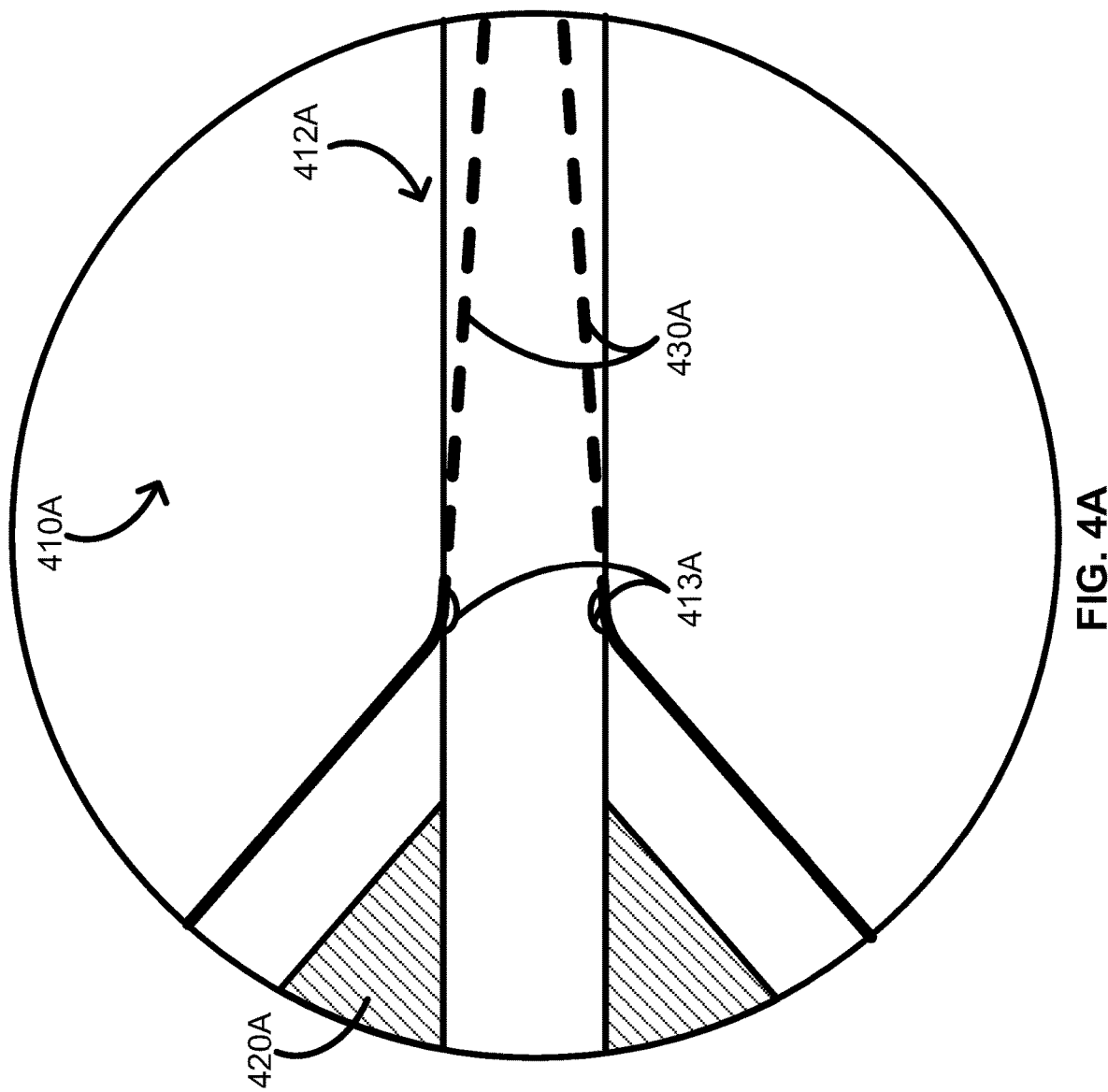

FIG. 4A provides a schematic illustrating at least a pair of scoring wires in a polymeric portion of a balloon catheter in accordance with some embodiments.

Figure 4B:
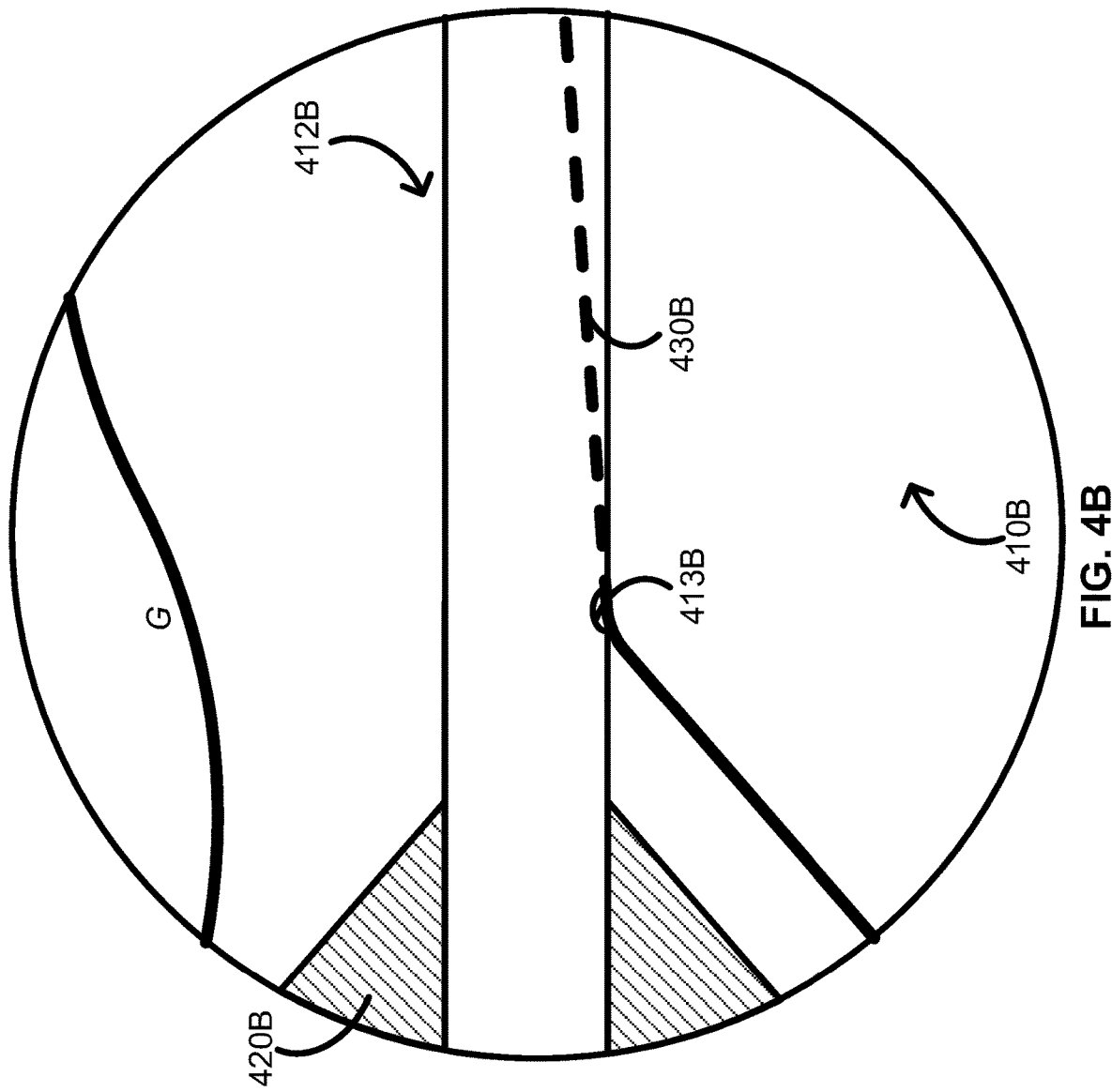

FIG. 4B provides a schematic illustrating a scoring wire in a polymeric portion of a balloon catheter in accordance with some embodiments.

Figure 5A:
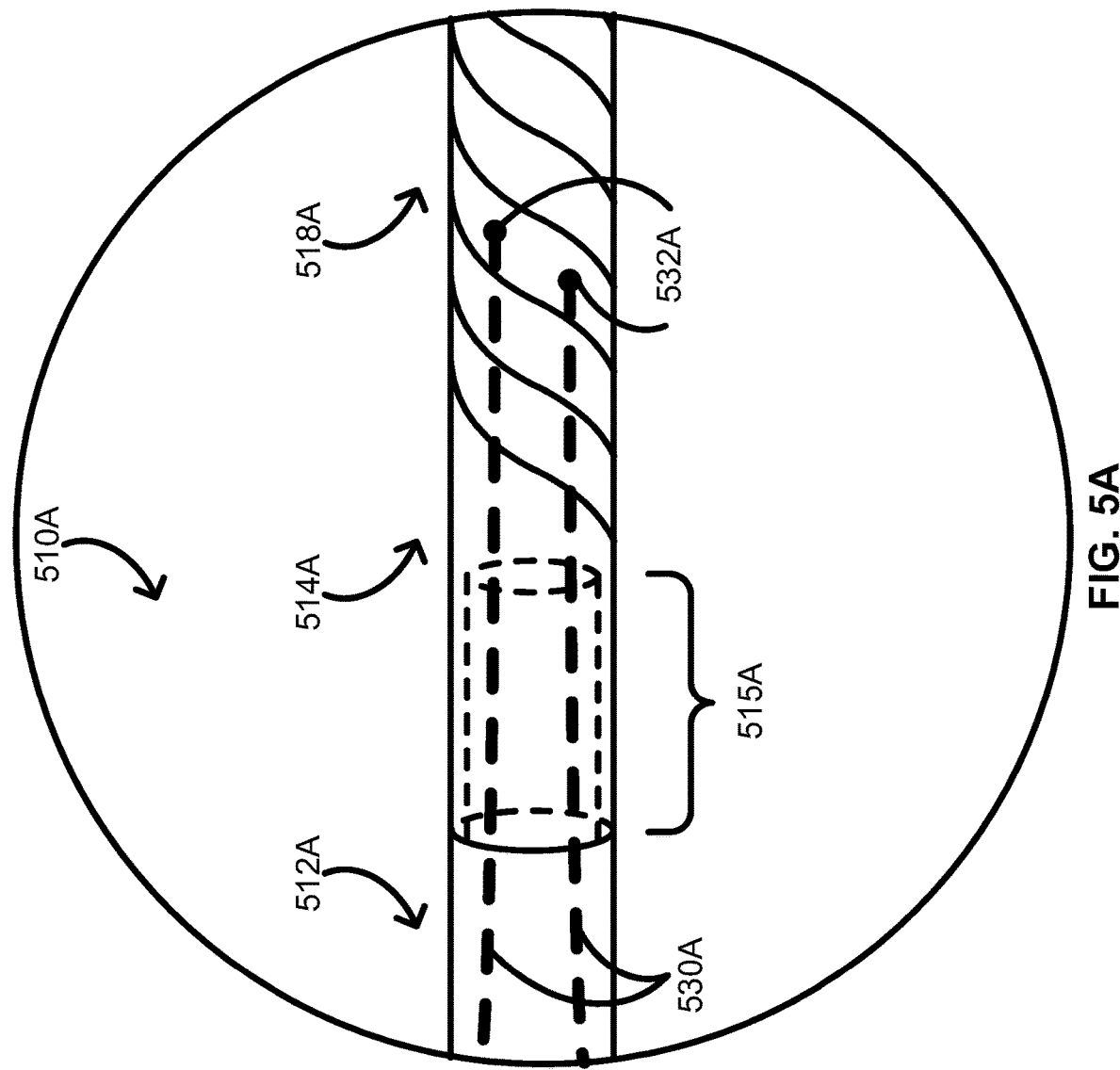

FIG. 5A provides a schematic illustrating at least a pair of scoring wires fixed to an internal surface of a spiral-cut portion of a balloon catheter in accordance with some embodiments.

Figure 5B:
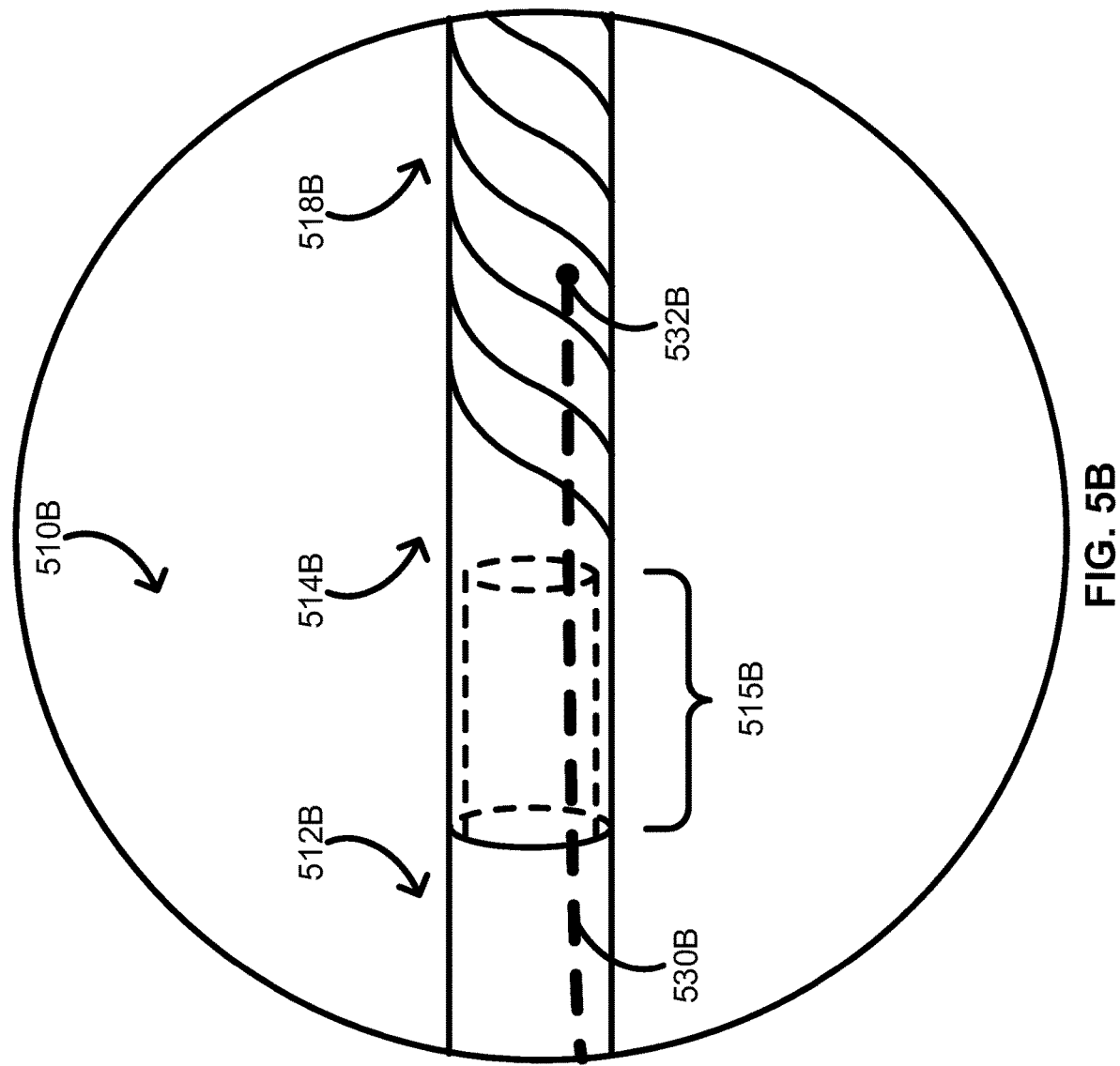

FIG. 5B provides a schematic illustrating a scoring wire fixed to an internal surface of a spiral-cut portion of a balloon catheter in accordance with some embodiments.

Figure 5C:
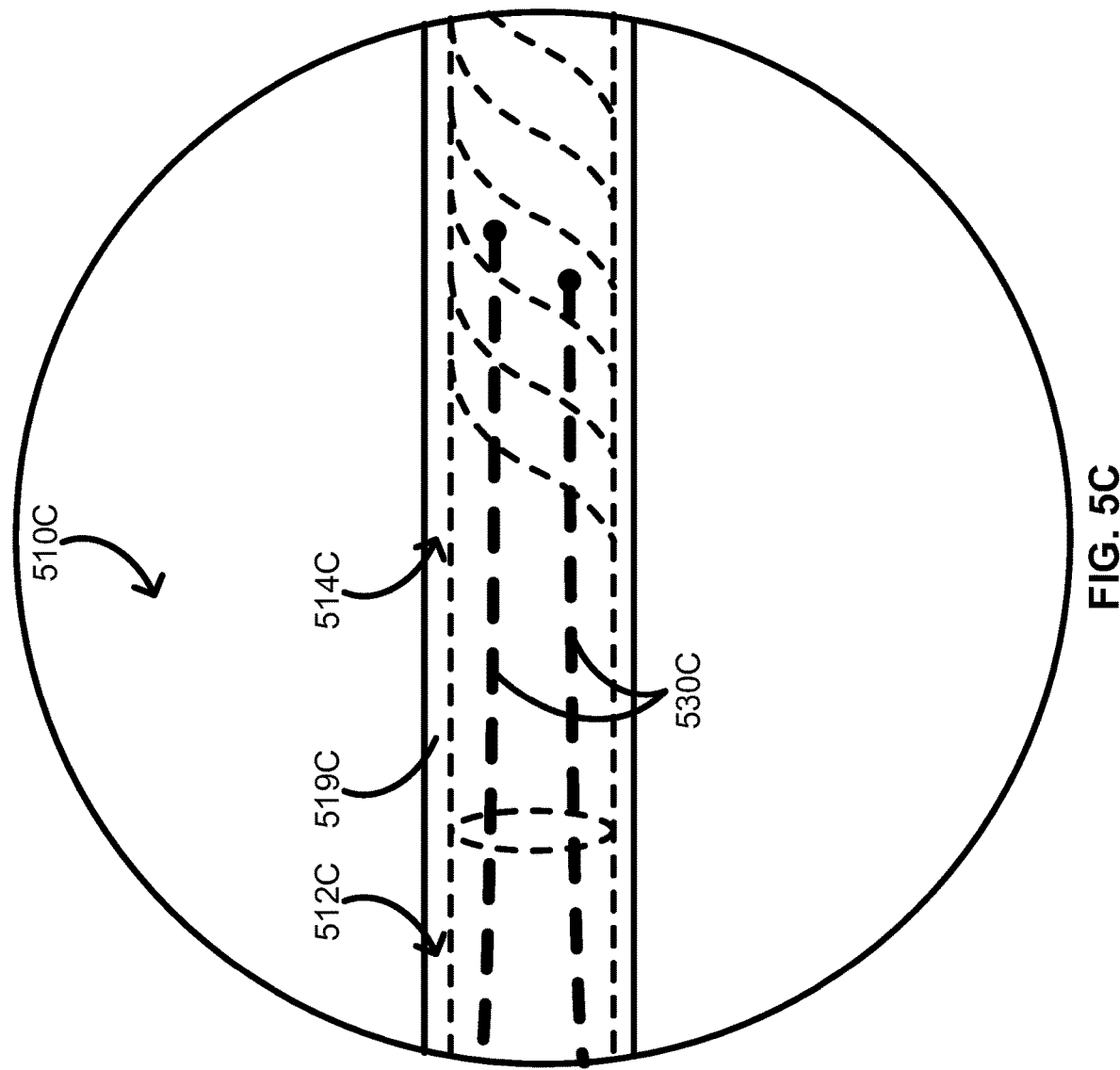

FIG. 5C provides a schematic illustrating a coupler formed over a polymeric portion and a metallic portion of a balloon catheter in accordance with some embodiments.

Figure 6A:
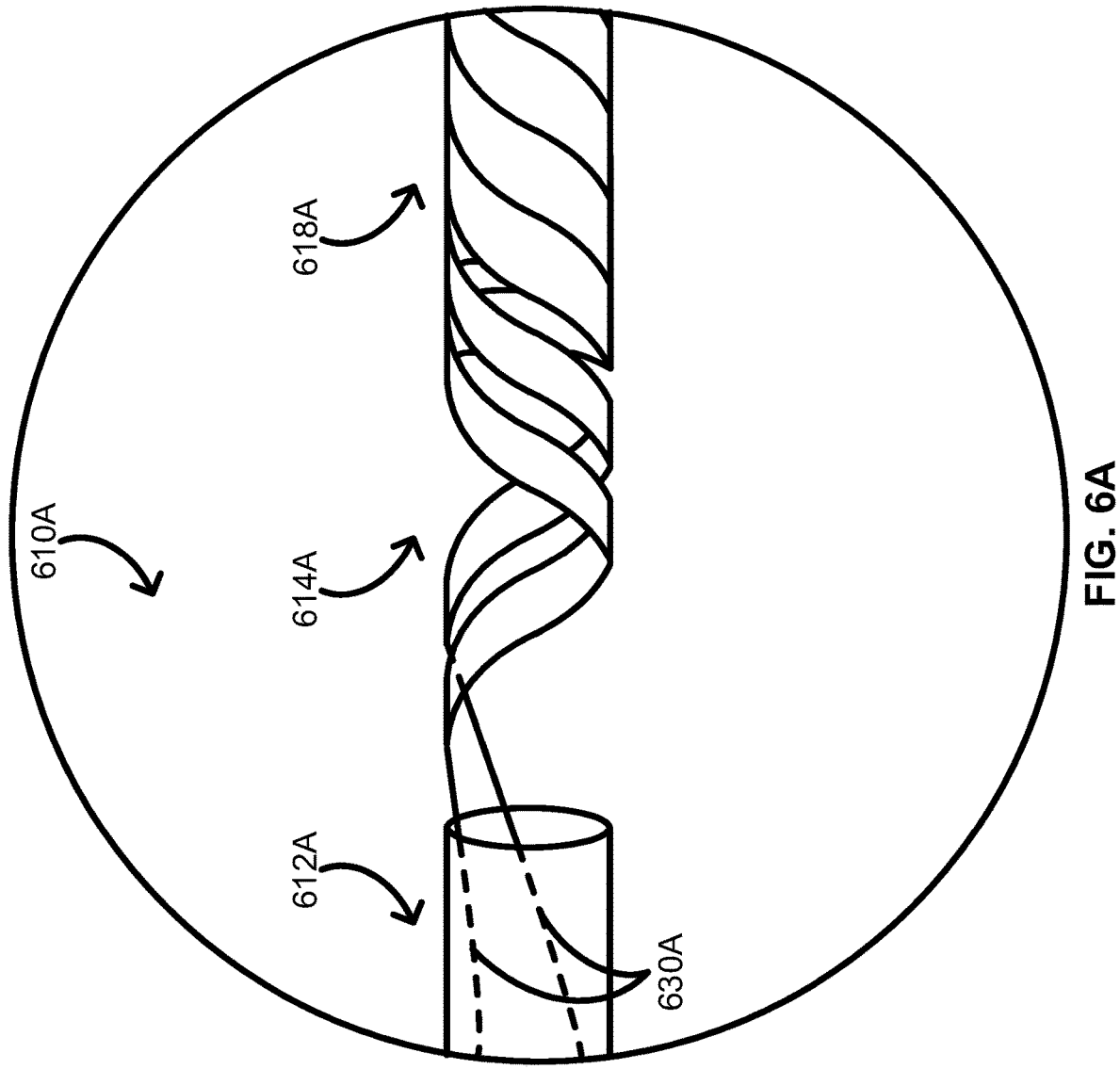

FIG. 6A provides a schematic illustrating at least a pair of scoring wires formed from a spiral-cut portion of a balloon catheter in accordance with some embodiments.

Figure 6B:
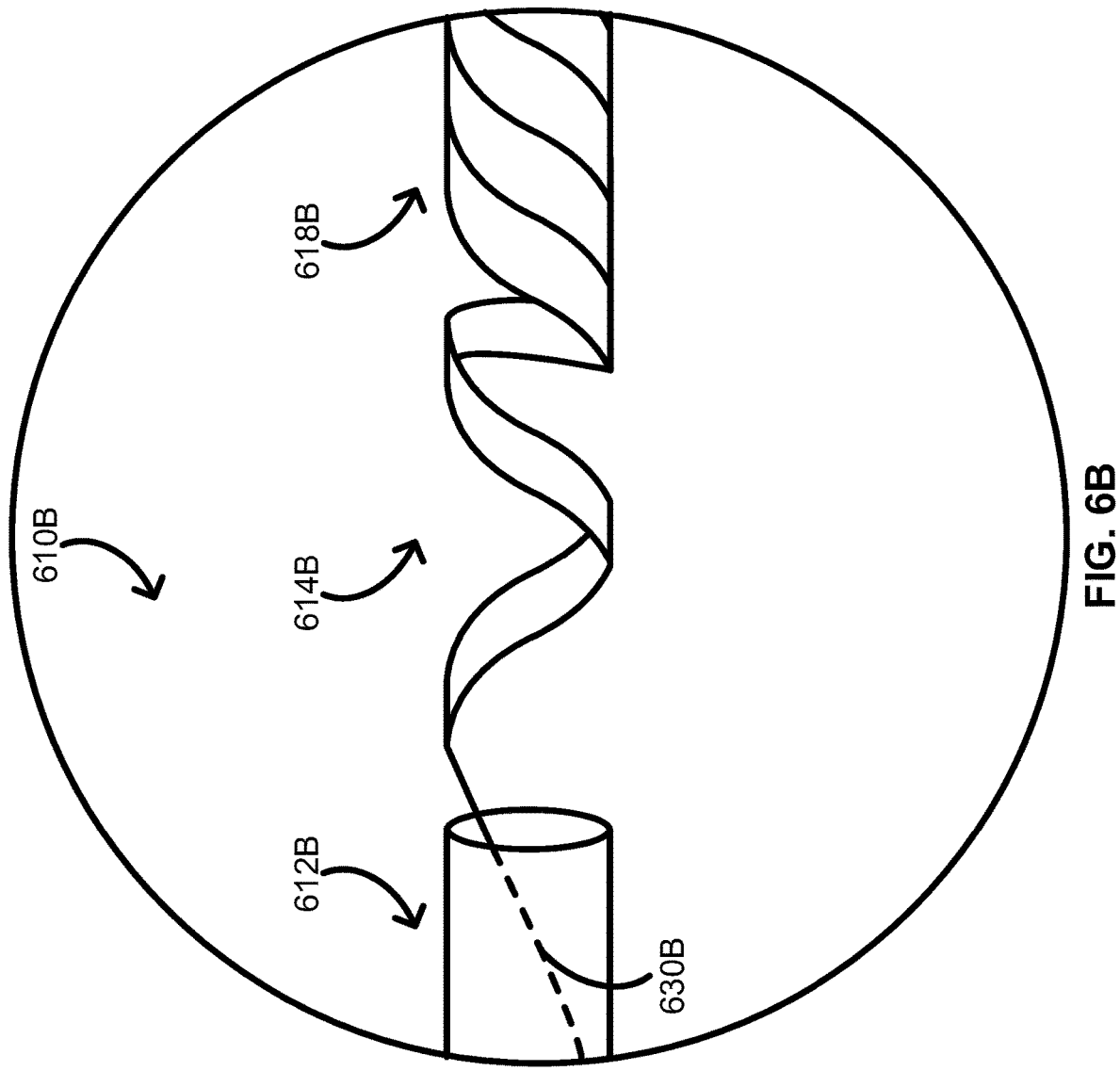

FIG. 6B provides a schematic illustrating a scoring wire formed from a spiral-cut portion of a balloon catheter in accordance with some embodiments.

Figure 6C:
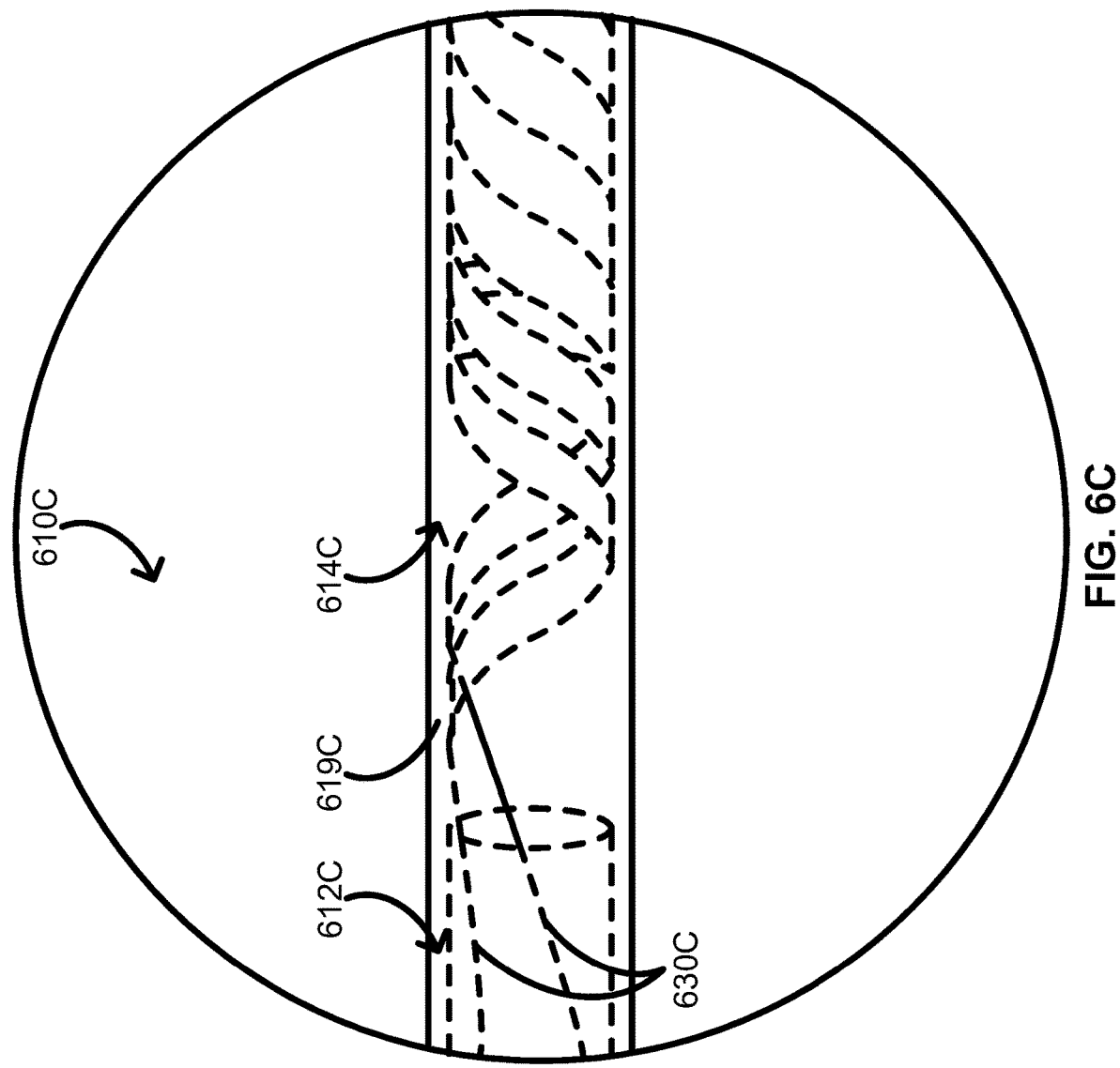

FIG. 6C provides a schematic illustrating a coupler formed over a polymeric portion and a metallic portion of a balloon catheter in accordance with some embodiments.

FIG. 7 provides a schematic illustrating modification of an intravascular lesion in accordance with some embodiments.

DETAILED DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by those of ordinary skill in the art.

Atherosclerosis is characterized by one or more intravascular lesions formed in part of plaque including blood-borne substances such as fat, cholesterol, and calcium. Surgical procedures for atherosclerosis such as balloon angioplasty can be used to restore patency and blood flow lost to the one or more intravascular lesions. Because early balloons could cause wall trauma by non-uniformly unfolding during inflation, changes have been made to balloon catheters to control balloon inflation and the forces imparted thereby. However, such changes are often not isolated to the balloons of such balloon catheters. Other balloon-catheter components and the performance thereof can be affected as well. Accordingly, there is a need to control balloon inflation and the forces imparted thereby while maintaining integrity in other balloon-catheter components. Provided herein in some embodiments are systems and methods that address the foregoing.

For example, in some embodiments, a catheter includes an elongate body with a polymeric portion and a metallic portion; a balloon over at least some of the polymeric portion; a coupler formed over or between the polymeric and metallic portions; and one or more scoring wires. The metallic portion can include a spiral-cut portion configured to prevent elongation and kinking of the elongate body. The one or more scoring wires can be fixed to and extend from a tip at a distal end of the elongate body, over the balloon, through the polymeric portion of the elongate body, through the coupler, and to the metallic portion of the elongate body. The one or more scoring wires can be fixed to an internal surface of the spiral-cut portion or formed from the spiral-cut portion.

Over-the-Wire Balloon Catheter

FIGS. 1, 4A, and 5A provide schematics illustrating an over-the-wire balloon catheter 100 including at least a pair of scoring wires 130 in accordance with some embodiments.

As shown in FIG. 1, the over-the-wire balloon catheter 100 can include an elongate body 110 with a polymeric portion 112 and a metallic portion 114, a balloon 120 over at least some of the polymeric portion 112 of the elongate body 110, and the one or more scoring wires 130. The over-the-wire balloon catheter 100 can further include a tip 116 at a distal end of the elongate body 110. In addition, the over-the-wire balloon catheter 100 can be configured with a guidewire G as shown entering the over-the-wire balloon catheter 100 through a guidewire port 142 in a hub 140 of the over-the-wire balloon catheter 100. The hub 140 can also include an inflation port 144 for attaching an inflation device for controlled inflation and deflation of the balloon 120.

As shown in FIG. 4A, the over-the-wire balloon catheter 100 can include one or more scoring wire ports 413A respectively for the one or more scoring wires 430A. The one or more scoring wire ports 413A can be located in the polymeric portion 412A of the elongate body 410A on a proximal side of the balloon 420A.

As shown in FIG. 5A, the over-the-wire balloon catheter 100 can include a coupler 515A formed between the polymeric portion 512A and the metallic portion 514A of the elongate body 510A. A proximal end of the polymeric portion 512A of the elongate body 510A can form a male-end connector of the coupler 515A, and a distal end of the metallic portion 514A of the elongate body 510A can form a female-end connector of the coupler 515A—or vice-versa. The metallic portion 514A of the elongate body 510A can include a spiral-cut portion 518A configured to act as a spring mechanism to prevent elongation and kinking of the elongate body 510A. The one or more scoring wires 530A can be fixed respectively at one or more fixation points 532A on an internal surface of the metallic portion 514A of the elongate body 510A such as an internal surface of the spiral-cut portion 518A of the elongate body 510A.

Rapid-Exchange Balloon Catheter

FIGS. 2, 4A, and 5A provide schematics illustrating a rapid-exchange balloon catheter 200 including at least a pair of scoring wires 230 in accordance with some embodiments.

As shown in FIG. 2, the rapid-exchange balloon catheter 200 can include an elongate body 210 with a polymeric portion 212 and a metallic portion 214, a balloon 220 over at least some of the polymeric portion 212 of the elongate body 210, and the one or more scoring wires 230. The rapid-exchange balloon catheter 200 can further include a tip 216 at a distal end of the elongate body 210 and a hub 240 with an inflation port 244 at a proximal end of the elongate body 210. In addition, the rapid-exchange balloon catheter 200 can be configured with a guidewire G as shown entering the rapid-exchange balloon catheter 200 through a guidewire port 242 of the rapid-exchange balloon catheter 200. The guidewire port 242 can be in the polymeric portion 212 of the elongate body 210.

As shown in FIG. 4A, the rapid-exchange balloon catheter 200 can include one or more scoring wire ports 413A respectively for the one or more scoring wires 430A. The one or more scoring wire ports 413A can be located in the polymeric portion 412A of the elongate body 410A on a proximal side of the balloon 420A.

As shown in FIG. 5A, the rapid-exchange balloon catheter 200 can include a coupler 515A formed between the polymeric portion 512A and the metallic portion 514A of the elongate body 510A. A proximal end of the polymeric portion 512A of the elongate body 510A can form a male-end connector of the coupler 515A, and a distal end of the metallic portion 514A of the elongate body 510A can form a female-end connector of the coupler 515A—or vice-versa. The metallic portion 514A of the elongate body 510A can include a spiral-cut portion 518A configured to act as a spring mechanism to prevent elongation and kinking of the elongate body 510A. The one or more scoring wires 530A can be fixed respectively at one or more fixation points 532A on an internal surface of the metallic portion 514A of the elongate body 510A such as an internal surface of the spiral-cut portion 518A of the elongate body 510A.

Short Rapid-Exchange Balloon Catheter (1)

FIGS. 3A, 4A, and 5A provide schematics illustrating a short rapid-exchange balloon catheter 300A including at least a pair of scoring wires 330A in accordance with some embodiments.

As shown in FIG. 3A, the short rapid-exchange balloon catheter 300A can include an elongate body 310A with a polymeric portion 312A and a metallic portion 314A, a balloon 320A over at least some of the polymeric portion 312A of the elongate body 310A, and the one or more scoring wires 330A. The short rapid-exchange balloon catheter 300A can further include a tip 316A at a distal end of the elongate body 310A and a hub 340A with an inflation port 344A at a proximal end of the elongate body 310A. In addition, the short rapid-exchange balloon catheter 300A can be configured with a guidewire G entering the short rapid-exchange balloon catheter 300A through a guidewire port 342A in the tip 316A of the short rapid-exchange balloon catheter 300A.

As shown in FIG. 4A, the short rapid-exchange balloon catheter 300A can include one or more scoring wire ports 413A respectively for the one or more scoring wires 430A. The one or more scoring wire ports 413A can be located in the polymeric portion 412A of the elongate body 410A on a proximal side of the balloon 420A.

As shown in FIG. 5A, the short rapid-exchange balloon catheter 300A can include a coupler 515A formed between the polymeric portion 512A and the metallic portion 514A of the elongate body 510A. A proximal end of the polymeric portion 512A of the elongate body 510A can form a male-end connector of the coupler 515A, and a distal end of the metallic portion 514A of the elongate body 510A can form a female-end connector of the coupler 515A—or vice-versa. The metallic portion 514A of the elongate body 510A can include a spiral-cut portion 518A configured to act as a spring mechanism to prevent elongation and kinking of the elongate body 510A. The one or more scoring wires 530A can be fixed respectively at one or more fixation points 532A on an internal surface of the metallic portion 514A of the elongate body 510A such as an internal surface of the spiral-cut portion 518A of the elongate body 510A.

Short Rapid-Exchange Balloon Catheter (2)

FIGS. 3B, 4B, and 5B provide schematics illustrating a short rapid-exchange balloon catheter 300B including a scoring wire 330B and a guidewire G in accordance with some embodiments.

As shown in FIG. 3B, the short rapid-exchange balloon catheter 300B can include an elongate body 310B with a polymeric portion 312B and a metallic portion 314B, a balloon 320B over at least some of the polymeric portion 312B of the elongate body 310B, the scoring wire 330B, and the guidewire G configured to function as an additional scoring wire. The short rapid-exchange balloon catheter 300B can further include a tip 316B at a distal end of the elongate body 310B and a hub 340B with an inflation port 344B at a proximal end of the elongate body 310B. In addition, the guidewire G can enter the short rapid-exchange balloon catheter 300B through a guidewire port 342B in the tip 316B of the short rapid-exchange balloon catheter 300B and pass over the balloon 320B as the additional scoring wire.

As shown in FIG. 4B, the short rapid-exchange balloon catheter 300B can include a scoring wire port 413B for the scoring wire 430B. The scoring wire port 413B can be located in the polymeric portion 412B of the elongate body 410B on a proximal side of the balloon 420B. While additional scoring wire ports are not excluded, additional scoring wire ports are not needed in the polymeric portion 412B of the elongate body 410B on account of the guidewire G and its function as the additional scoring wire.

As shown in FIG. 5B, the short rapid-exchange balloon catheter 300B can include a coupler 515B formed between the polymeric portion 512B and the metallic portion 514B of the elongate body 510B. A proximal end of the polymeric portion 512B of the elongate body 510B can form a male-end connector of the coupler 515B, and a distal end of the metallic portion 514B of the elongate body 510B can form a female-end connector of the coupler 515B—or vice-versa. The metallic portion 514B of the elongate body 510B can include a spiral-cut portion 518B configured to act as a spring mechanism to prevent elongation and kinking of the elongate body 510B. The scoring wire 530B can be fixed at a fixation point 532B on an internal surface of the metallic portion 514B of the elongate body 510B such as an internal surface of the spiral-cut portion 518B of the elongate body 510B.

Scoring Wires (1)

Each of the one or more scoring wires can be separately formed and subsequently fixed by its free ends to a catheter.

As shown in FIGS. 1, 2, and 3A, the one or more scoring wires of the over-the-wire balloon catheter 100, the rapid-exchange balloon catheter 200, and the short rapid-exchange balloon catheter 300A, respectively, can extend from the tip at the distal end of the elongate body and over the balloon. As shown in FIG. 4A, the one or more scoring wires 430A can extend through the polymeric portion 412A of the elongate body 410A. As shown in FIG. 5A, the one or more scoring wires 530A can extend through at least a first coupler such as the coupler 515A, and to the metallic portion 514A of the elongate body. For example, each scoring wire of a pair of scoring wires can extend from the tip at the distal end of the elongate body, over an opposing side of the balloon, through a scoring wire port in an opposing side of the polymeric portion of the elongate body, through at least a portion of a lumen of the polymeric portion of the elongate body, through a lumen of the coupler, and into a lumen of the metallic portion of the elongate body. The one or more scoring wires can be fixed to the tip of the elongate body (see FIGS. 1, 2, and 3A respectively for the over-the-wire balloon catheter 100, the rapid-exchange balloon catheter 200, and the short rapid-exchange balloon catheter 300A) as well as an internal surface of the metallic portion of the elongate body proximate to the coupler (FIG. 5A). The internal surface of the metallic portion of the elongate body to which each scoring wire of the one or more scoring wires can be fixed can be a luminal surface of the spiral-cut portion of the metallic portion of the elongate body.

As shown in FIG. 3B, the scoring wire 330B of the short rapid-exchange balloon catheter 300B can extend from the tip at the distal end of the elongate body 310B and over the balloon 320B. When present, the guidewire G can also extend from the guidewire port in the tip 316B at the distal end of the elongate body 310B and over the balloon 320B. As shown in FIG. 4B, the scoring wire 430B can extend through the polymeric portion 412B of the elongate body 410B. As shown in FIG. 5B, the scoring wire 530B can extend through at least a first coupler such as the coupler 515B, and to the metallic portion 514B of the elongate body 510B. For example, the scoring wire 530B can extend from the tip 316B (FIG. 3B) at the distal end of the elongate body 510B, over an opposing side of the balloon 320B (FIG. 3B) from the guidewire G, when present, through a scoring wire port in the polymeric portion 512B of the elongate body 510B, through at least a portion of a lumen of the polymeric portion 512B of the elongate body 510B, through a lumen of the coupler 515B, and into a lumen of the metallic portion 514B of the elongate body 510B. The scoring wire 530B can be fixed to the tip 316B (FIG. 3B) of the elongate body 510B as well as an internal surface of the metallic portion 514B of the elongate body 510B proximate to the coupler 515B (FIG. 5B). The internal surface of the metallic portion 514B of the elongate body 510B to which the scoring wire 530B can be fixed can be a luminal surface of the spiral-cut portion of the metallic portion 514B of the elongate body 510B.

Following on the foregoing, the one or more scoring wires 530A of FIG. 5A or the scoring wire 530B of FIG. 5B can further extend through a second coupler 519C shown in FIG. 5C for the one or more scoring wires 530C. The second coupler 519C can include a polymeric sleeve over the polymeric portion 512C and the metallic portion 514C of the elongate body 510C, and, thus, over the coupler 515C (not shown) as well. The polymeric sleeve can be a heat-shrunken polymeric sleeve of a biocompatible material such as polytetrafluoroethylene ("PTFE").

The manner in which the one or more scoring wires 530A are fixed to the tip 316A (FIG. 3A) of the elongate body 510A and the internal surface of the metallic portion 514A of the elongate body 510A is not limited. For example, a spot weld such as a laser spot weld can fix each of the one or more scoring wires 530A to at least the internal surface of the metallic portion 514A of the elongate body 510A. When the guidewire G is used as a scoring wire in the short rapid-exchange balloon catheter 300B, the guidewire G is not fixed to the tip 316B (FIG. 3B) of the elongate body 510B or the internal surface of the metallic portion 514B of the elongate body 510B.

At least one scoring wire of the one or more scoring wires can include radiopaque markers configured for radiographic delineation of a working length of the balloon.

Scoring Wires (2)

Each of the one or more scoring wires can be formed from the spiral-cut portion of the metallic portion of the elongate body and subsequently fixed by its free end to a catheter.

As shown in FIGS. 1, 2, and 3A, the one or more scoring wires of the over-the-wire balloon catheter 100, the rapid-exchange balloon catheter 200, and the short rapid-exchange balloon catheter 300A, respectively, can extend from the tip at the distal end of the elongate body and over the balloon. As shown in FIG. 4A, the one or more scoring wires 430A can extend through the polymeric portion 412A of the elongate body 410A. As shown in FIG. 6A, the one or more scoring wires 630A can emerge from the polymeric portion 612A and form into the spiral-cut portion 618A of the metallic portion 614A of the elongate body 610A. For example, each scoring wire of a pair of scoring wires can extend from the tip at the distal end of the elongate body, over an opposing side of the balloon, through a scoring wire port in an opposing side of the polymeric portion of the elongate body, through at least a portion of a lumen of the polymeric portion of the elongate body, and form into the spiral-cut portion of the metallic portion of the elongate body. The one or more scoring wires can be drawn out or otherwise formed from the spiral-cut portion and fixed to the tip of the elongate body (see FIGS. 1, 2, and 3A respectively for the over-the-wire balloon catheter 100, the rapid-exchange balloon catheter 200, and the short rapid-exchange balloon catheter 300A).

The one or more scoring wires 630A can be formed from the metallic portion 614A respectively with one or more spiral cuts in the metallic portion 614A. As shown in FIG. 6A, for example, two longitudinally offset spiral cuts provides two scoring wires.

As shown in FIG. 3B, the scoring wire 330B of the short rapid-exchange balloon catheter 300B can extend from the tip at the distal end of the elongate body 310B and over the balloon 320B. When present, the guidewire G can also extend from the guidewire port in the tip 316B at the distal end of the elongate body 310B and over the balloon 320B. As shown in FIG. 4B, the scoring wire 430B can extend through the polymeric portion 412B of the elongate body 410B. As shown in FIG. 6B, the scoring wire 630B can emerge from the polymeric portion 612B and form into the spiral-cut portion 618B of the metallic portion 614B of the elongate body 610B. For example, the scoring wire 630B can extend from the tip 316B (FIG. 3B) at the distal end of the elongate body 610B, over an opposing side of the balloon 320B (FIG. 3B) from the guidewire G, when present, through a scoring wire port in the polymeric portion 412B (FIG. 4B) of the elongate body 610B, through at least a portion of a lumen of the polymeric portion 612B of the elongate body 610B, and form into the spiral-cut portion 618B of the metallic portion 614B of the elongate body 610B. The scoring wire can be drawn out or otherwise formed from the spiral-cut portion and fixed to the tip of the elongate body (see FIGS. 1, 2, and 3A respectively for the over-the-wire balloon catheter 100, the rapid-exchange balloon catheter 200, and the short rapid-exchange balloon catheter 300A).

Following on the foregoing, the one or more scoring wires 630A of FIG. 6A or the scoring wire 630B of FIG. 6B can further extend through a coupler 619C shown in FIG. 6C for the one or more scoring wires 630C. The coupler 619C can include a polymeric sleeve over the polymeric portion 612C and the metallic portion 614C of the elongate body 610C. The polymeric sleeve can be a heat-shrunken polymeric sleeve of a biocompatible material such as polytetrafluoroethylene ("PTFE").

The manner in which the one or more scoring wires 730A are fixed to the tip 316A (FIG. 3A) of the elongate body 710A is not limited. When the guidewire G is used as a scoring wire in the short rapid-exchange balloon catheter 300B, the guidewire G is not fixed to the tip 316B (FIG. 3B) of the elongate body 510B.

At least one scoring wire of the one or more scoring wires can include radiopaque markers configured for radiographic delineation of a working length of the balloon.

FIG. 7 provides a schematic illustrating modification of an intravascular lesion in accordance with some embodiments.

As shown, a balloon catheter such as the over-the-wire balloon catheter 100, the rapid-exchange balloon catheter 200, or one of the short rapid-exchange balloon catheters 300A or 300B can be advanced through a patient's vasculature until the balloon (e.g., the balloon 120) and the one or more scoring wires (e.g., the one or more scoring wires 130) are in a position alongside an intravascular lesion L. Inflation of the balloon in such a position provides outwardly focused forces $f_1$ and $f_2$ against the lesion L along the one or more scoring wires over a length of the balloon, thereby restoring patency lost to the intravascular L. The forces $f_1$ and $f_2$ can increase from a minimum when the balloon is in an uninflated or minimally inflated state to a maximum when the balloon is in a fully inflated state. The foregoing can be effected in vasculature of various sizes and tortuosities. The balloon and the one or more scoring wires are sufficiently flexible to modify intravascular lesions in curved vasculature.

A balloon catheter such as the over-the-wire balloon catheter 100, the rapid-exchange balloon catheter 200, or one of the short rapid-exchange balloon catheters 300A or 300B can be used to dilate stenoses in the iliac, femoral, ilio-femoral, popliteal, infra-popliteal, and renal arteries and to treat obstructive lesions of native or synthetic arteriovenous dialysis fistulae. The balloon catheter can also be used for post dilatation of balloon-expandable stents, self-expanding stents, and stent grafts in the peripheral vasculature.

Inflation Device

A balloon catheter such as the over-the-wire balloon catheter 100, the rapid-exchange balloon catheter 200, or one of the short rapid-exchange balloon catheters 300A or 300B can be used in a system with an inflation device configured to inflate the balloon of the balloon catheter. Such an inflation device can include a piston pump, a manometer, high-pressure tubing configured to tolerate pressures of at least 40 atm, and an adapter configured to connect with the hub at the proximal end of the elongate body of the balloon catheter. In some embodiments, the inflation device is a CALIBER® Inflation Device or the PRESTO® Inflation Device by Bard Peripheral Vascular, Inc. of Tempe, Ariz.

As such, provided herein in some embodiments is a catheter including an elongate body with a polymeric portion and a metallic portion, a balloon over at least some of the polymeric portion of the elongate body, a coupler formed between the polymeric and metallic portions of the elongate body, and one or more scoring wires. The one or more scoring wires can extend from a tip at a distal end of the elongate body, over the balloon, through the polymeric portion of the elongate body, through the coupler, and to the metallic portion of the elongate body. The one or more scoring wires can be fixed to the tip of the elongate body as well as an internal surface of the metallic portion of the elongate body proximate to the coupler. The internal surface of the metallic portion of the elongate body to which each scoring wire of the pair of scoring wires can be fixed can be a luminal surface of a spiral-cut portion of the metallic portion of the elongate body.

In such embodiments, the metallic portion of the elongate body can include a spiral-cut portion configured to act as a spring mechanism to prevent elongation and kinking of the spiral-cut portion. In such embodiments, a proximal end of the polymeric portion of the elongate body can form a male-end connector of the coupler, and a distal end of the metallic portion of the elongate body can form a female-end connector of the coupler. In such embodiments, the one or more scoring wires can be at least a pair of scoring wires, and each scoring wire of the pair of scoring wires can pass over an opposing side of the balloon. In such embodiments, each scoring wire of the pair of scoring wires can pass through a scoring wire port in an opposing side of the polymeric portion of the elongate body as well as at least a portion of a lumen of the polymeric portion of the elongate body. In such embodiments, each scoring wire of the pair of scoring wires can further pass through a lumen of the coupler as well as at least a portion of a lumen of the metallic portion of the elongate body. In such embodiments, at least one scoring wire of the one or more scoring wires can include radiopaque markers configured for radiographic delineation of a working length of the balloon. In such embodiments, the one or more scoring wires can be configured to provide an outwardly focused force along a length of the balloon when the balloon is in an inflated state even at a low inflation level. In such embodiments, the one or more scoring wires and the balloon can be sufficiently flexible to modify intravascular lesions in curved vasculature when the balloon is in an inflated state. In such embodiments, the catheter can be configured as an over-the-wire catheter with a guidewire port in a hub at a proximal end of the elongate body. In such embodiments, the catheter can be configured as a rapid-exchange catheter with a guidewire port in the polymeric portion of the elongate body between the balloon and the coupler. In such embodiments, the catheter can be configured as a short rapid-exchange catheter with a guidewire port in the tip of the elongate body.

Also provided herein in some embodiments is a catheter including an elongate body with a polymeric portion and a metallic portion; a balloon over at least some of the polymeric portion of the elongate body; a coupler over the polymeric and metallic portions of the elongate body; and one or more scoring wires. The metallic portion of the elongate body can include a spiral-cut portion configured to prevent elongation and kinking of the elongate body. The coupler can include a heat-shrunken polymeric sleeve. The one or more scoring wire can extend from a tip at a distal end of the elongate body, over the balloon, through the polymeric portion, through the coupler, and to the metallic portion. The one or more scoring wires can be formed from the spiral-cut portion of the metallic portion and fixed to the tip at the distal end of the elongate body.

In such embodiments, each wire of the one or more scoring wire results from a separate spiral cut longitudinally offset from any other spiral cut in the spiral-cut portion.

Also provided herein in some embodiments is a catheter including an elongate body including a polymeric portion and a metallic portion, a balloon over at least some of the polymeric portion of the elongate body, a coupler formed between the polymeric and metallic portions of the elongate body, and at least a pair of scoring wires. The metallic portion of the elongate body can include a spiral-cut portion configured to act as a spring mechanism to prevent elongation and kinking of the spiral-cut portion. The coupler can include a male-end connector and a female-end connector, wherein the male-end connector can be formed from a proximal end of the polymeric portion of the elongate body, and wherein the female-end connector can be formed from a distal end of the metallic portion of the elongate body. Each scoring wire of the pair of scoring wires can extend from a tip at a distal end of the elongate body, over an opposing side of the balloon, through a scoring wire port in an opposing side of the polymeric portion of the elongate body, through a lumen of the polymeric portion of the elongate body, through a lumen of the coupler, and into a lumen of the metallic portion of the elongate body. The one or more scoring wires can be fixed to the tip of the elongate body as well as an internal surface of the spiral-cut portion of the elongate body proximate to the coupler.

In such embodiments, the one or more scoring wires can be configured to provide an outwardly focused force along a length of the balloon when the balloon is in an inflated state even at a low inflation level. In such embodiments, the one or more scoring wires and the balloon can be sufficiently flexible to modify intravascular lesions in curved vasculature when the balloon is in an inflated state. In such embodiments, at least one scoring wire of the one or more scoring wires can include radiopaque markers configured for radiographic delineation of a working length of the balloon. In such embodiments, the catheter can be configured as a rapid-exchange catheter with a guidewire port in the polymeric portion of the elongate body between the balloon and the coupler. In such embodiments, the catheter can be configured as a short rapid-exchange catheter with a guidewire port in the tip of the elongate body, and the guidewire through the guidewire port can be one scoring wire of the pair of scoring wires.

Also provided herein in some embodiments is a system including a catheter and an inflation device. The catheter can include an elongate body with a polymeric portion and a metallic portion, a balloon over at least some of the polymeric portion of the elongate body, a coupler formed between the polymeric and metallic portions of the elongate body, and one or more scoring wires. The metallic portion of the elongate body can include a spiral-cut portion configured to act as a spring mechanism to prevent elongation and kinking of the elongate body. The one or more scoring wire can extend from a tip at a distal end of the elongate body, over the balloon, through the polymeric portion of the elongate body, through the coupler, and to the metallic portion of the elongate body. The one or more scoring wires can be fixed to the tip of the elongate body as well as an internal surface of the spiral-cut portion of the elongate body proximate to the coupler. The inflation device can be configured to inflate the balloon of the catheter.

In such embodiments, the inflation device can include a piston pump, a manometer, high-pressure tubing configured to tolerate pressures of at least 40 atm, and an adapter configured to connect with a hub at a proximal end of the elongate body of the catheter.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A catheter, comprising:
   an elongate body including a polymeric portion and a metallic portion;
   a balloon over at least some of the polymeric portion;
   a coupler formed between the polymeric and metallic portions; and
   one or more scoring wires extending from a tip at a distal end of the elongate body, over the balloon, through the polymeric portion, through the coupler, and to the metallic portion, wherein the one or more scoring wires are fixed to the tip and an internal surface of the metallic portion proximate to the coupler.

2. The catheter according to claim 1, wherein the metallic portion includes a spiral-cut portion configured to prevent elongation and kinking of the spiral-cut portion.

3. The catheter according to claim 1, wherein:
   a proximal end of the polymeric portion forms a male-end connector of the coupler; and
   a distal end of the metallic portion forms a female-end connector of the coupler.

4. The catheter according to claim 1, wherein:
   the one or more scoring wires are at least a pair of scoring wires, and
   each scoring wire of the pair of scoring wires passes over an opposing side of the balloon.

5. The catheter according to claim 4, wherein each scoring wire of the pair of scoring wires passes through a scoring wire port in an opposing side of the polymeric portion and at least a portion of a lumen of the polymeric portion.

6. The catheter according to claim 4, wherein:
   each scoring wire of the pair of scoring wires further passes through a lumen of the coupler and at least a portion of a lumen of the metallic portion; and
   the internal surface of the metallic portion to which each scoring wire of the pair of scoring wires is fixed is a luminal surface of a spiral-cut portion of the metallic portion.

7. The catheter according to claim 1, wherein at least one scoring wire of the one or more scoring wires includes radiopaque markers configured for radiographic delineation of a working length of the balloon.

8. The catheter according to claim 1, wherein the one or more scoring wires are configured to provide an outwardly focused force along a length of the balloon when the balloon is in an inflated state.

9. The catheter according to claim 1, wherein the one or more scoring wires and the balloon are sufficiently flexible to modify intravascular lesions in curved vasculature when the balloon is in an inflated state.

10. The catheter according to claim 1, wherein the catheter is configured as an over-the-wire catheter with a guidewire port in a hub at a proximal end of the elongate body.

11. The catheter according to claim 1, wherein the catheter is configured as a rapid-exchange catheter with a guidewire port in the polymeric portion between the balloon and the coupler.

12. The catheter according to claim 1, wherein the catheter is configured as a short rapid-exchange catheter with a guidewire port in the tip.

13. A catheter, comprising:
    an elongate body including a polymeric portion and a metallic portion;
    a balloon over at least some of the polymeric portion;
    a coupler over the polymeric and metallic portions,
       wherein the coupler is a heat-shrunken polymeric sleeve; and
    one or more scoring wires extending from a tip at a distal end of the elongate body, over the balloon, through the polymeric portion, through the coupler, and to the metallic portion,
       wherein the one or more scoring wires are formed from a spiral-cut portion of the metallic portion and fixed to the tip at a distal end of the elongate body.

14. The catheter according to claim 13, wherein each wire of the one or more scoring wire results from a separate spiral cut in the spiral-cut portion.

15. A catheter, comprising:
    an elongate body including a polymeric portion and a metallic portion, wherein the metallic portion includes a spiral-cut portion configured to prevent elongation and kinking of the spiral-cut portion;
    a balloon over at least some of the polymeric portion;
    a coupler formed between the polymeric and metallic portions, wherein
       a proximal end of the polymeric portion forms a male-end connector of the coupler; and
       a distal end of the metallic portion forms a female-end connector of the coupler; and
    at least a pair of scoring wires, wherein:
       each scoring wire of the pair of scoring wires extends from a tip at a distal end of the elongate body, over an opposing side of the balloon, through a scoring wire port in an opposing side of the polymeric portion, through a lumen of the polymeric portion, through a lumen of the coupler, and into a lumen of the metallic portion; and
       the scoring wires are fixed to the tip and an internal surface of the spiral-cut portion proximate to the coupler.

16. The catheter according to claim 15, wherein the one or more scoring wires are configured to provide an outwardly focused force along a length of the balloon when the balloon is in an inflated state.

17. The catheter according to claim 15, wherein the one or more scoring wires and the balloon are sufficiently flexible to modify intravascular lesions in curved vasculature when the balloon is in an inflated state.

18. The catheter according to claim 15, wherein at least one scoring wire of the one or more scoring wires includes radiopaque markers configured for radiographic delineation of a working length of the balloon.

19. The catheter according to claim 15, wherein the catheter is configured as a rapid-exchange catheter with a guidewire port in the polymeric portion between the balloon and the coupler.

20. The catheter according to claim 15, wherein:
   the catheter is configured as a short rapid-exchange catheter with a guidewire port in the tip; and
   a guidewire through the guidewire port is one scoring wire of the pair of scoring wires.

21. A system, comprising:
   a) a catheter including:
      an elongate body including a polymeric portion and a metallic portion, wherein the metallic portion includes a spiral-cut portion configured to prevent elongation and kinking of the elongate body;
      a balloon over at least some of the polymeric portion;
      a coupler formed between the polymeric and metallic portions; and
      one or more scoring wires extending from a tip at a distal end of the elongate body, over the balloon, through the polymeric portion, through the coupler, and to the metallic portion, wherein the one or more scoring wires are fixed to the tip and an internal surface of the spiral-cut portion proximate to the coupler; and
   b) an inflation device configured to inflate the balloon.

22. The system according to claim 21, wherein the inflation device comprises a piston pump, a manometer, high-pressure tubing configured to tolerate pressures of at least 40 atm, and an adapter configured to connect with a hub at a proximal end of the elongate body of the catheter.

* * * * *